United States Patent [19]

Schlossman

[11] 4,301,046

[45] Nov. 17, 1981

[54] UNIVERSAL NAIL POLISH USING POLYESTER RESIN

[75] Inventor: Mitchell L. Schlossman, Rockaway, N.J.

[73] Assignee: Tevco Inc.

[21] Appl. No.: 111,174

[22] Filed: Jan. 10, 1980

[51] Int. Cl.³ .............................................. C08L 1/10
[52] U.S. Cl. ......................................... 260/16; 424/61
[58] Field of Search ............................. 260/16; 424/61

[56] References Cited

U.S. PATENT DOCUMENTS

| | | | |
|---|---|---|---|
| 2,215,898 | 9/1940 | Anderson | 424/61 |
| 3,849,547 | 11/1974 | Kalopissis | 424/61 |
| 4,022,724 | 5/1977 | Kreuder et al. | 260/16 |

FOREIGN PATENT DOCUMENTS 41-11000  6/1966  Japan ..................................... 424/61

Primary Examiner—Maurice J. Welsh
Assistant Examiner—N. M. Nutter
Attorney, Agent, or Firm—Toren, McGeady & Stanger

[57] ABSTRACT

A nail polish is made from 92% to 96% ingredients including a film former, colorant, plasticizer and solvent; and 4% to 8% polyester resin made from 2,2,4-trimethyl-1, 3-pentanediol, isophthalic acid-85, and trimellitic anhydride, having an acid value of 75–85 and a viscosity of 125–175 centipoise. In another example, the polyester is made from 50.932% 2,2,4 trimethyl-1, 3-pentanediol, 27.579% isophthalic acid-85, 0.186% dibutyl tin oxide catalyst and 21.303 trimellitic anhydride, having an acid value of 80 and a viscosity of 150 centipoise.

29 Claims, No Drawings

UNIVERSAL NAIL POLISH USING POLYESTER RESIN

BACKGROUND OF THE INVENTION

This invention relates to nail polishes, and particularly, to hypo-allergenic nail polishes.

The chief requirements of a satisfactory nail enamel are that it should apply easily, be well adherent, dry and harden quickly, be glossy, waterproof and suitably colored, wear well, be elastic, resist chipping, peeling and abrasion for a reasonable period of time, and be dermatologically innocuous.

In general, the main constituents of a nail enamel are the film former, a resin, colorants, plasticizer and solvents.

Nail lacquer formulations have depended on nitrocellulose as its main film-forming ingredient for many years. Derived from cellulose, it provides an unusual combination of properties of toughness, durability, solubility, and solvent release.

Nitrocellulose must be neutral, for free acid could damage the fingernail and destroy the colors of the polish. The most commonly used viscosity grades of nitrocellulose are so-called RS ¼ sec., which has a high solids content, but poor wear resistance, RS ½ sec., which has better wear resistance and a reasonably high non-volatile content, and lastly, RS 5-6 sec. and RS 60-80 sec., which have higher viscosities than the RS ½ sec. grade.

The term RS refers to the RS brand of nitrocellulose with a nitrogen content of 11.2-12.8% with solubility in esters, ketones and glycol ethers manufactured by Hercules, Inc. The terms ¼ sec., ½ sec., 5-6 sec., etc. represent viscosity and refer to the time it takes for a ball to fall to a given depth in the material.

Nitrocellulose is supplied in 70% concentrations, wet with 30% ethyl or isopropyl alcohol. Fingernail polish grade nitrocellulose has a low moisture content. Resins are used in nitrocellulose compositions to improve their depth, gloss and adhesion. The most widely used modifying resin in nail enamel is the toluenesulfonamide/formaldehyde resin which provides excellent depth, gloss, flow and adhesion as well as good resistant films. Addition of this resin and others permits an increase in solids content without appreciably increasing lacquer viscosity. Nail enamels, using a minimum of coats, are more easily attained.

The solvent combinations used in nail lacquer technology usually consists of the alcohol which is used to wet the nitrocellulose, together with an active solvent such as butyl acetate and an aromatic hydrocarbon diluent such as toluene. Additionally, solvents used are diluents. Diluents are organic solvents that are miscible with the nitrocellulose solvents, but are not themselves solvents for nitrocellulose. They are used to reduce the cost of formulation and help to lower and stabilize the viscosity of the enamels. Alcohols, aromatic hydrocarbons and aliphatic hydrocarbons are the classes of diluents used. Ethyl (78° C.), isopropyl (82.3° C.), and butyl alcohol (118° C.) are the most efficient.

Most modern nail enamel formulations use a combination of camphor and another plasticizer. No one plasticizer possesses all the desirable properties necessary to obtain permanent extensibility and flexibility in the resulting films. Commonly used solvent-type plasticizers are dibutyl phthalate (bp 340° C.), dioctyl phthalate, diphenyl phthalate, camphor, dibutoxy ethyl phthalate, tricresyl phosphate (241°-255° C.), triphenyl phosphate and citrate plasticizers.

Colorants for nail enamel are usually confined to the non-bleeding in lacquer solvents. The most widely used pigments in opaque enamels are red organic pigments, D & C Red #6, #7, #9, #10, #30, #33, and #34 Lakes, D & C Yellow #5 Lakes, titanium dioxide, iron oxides used to produce brown and tan shades and iron black and iron blue. Basic Violet #1 and #3, D & C Red #17, D & C Violet #2 and D & C Red #19 dyes are the most widely used soluble dyes for transparent systems. Pigments with relatively high specific gravities such as titanium dioxide and the iron oxides are most widely used in "creme" shades and most responsible for pigment settling problems.

An example of one formulation in percentages by weight of the total composition (w/w%) is:

| | W/W % | |
|---|---|---|
| Nitrocellulose RS ½ sec.(dry) | 15.00 | film former |
| Santolite resin (1) | 12.00 | resin |
| Dibutyl phthalate | 3.00 | plasticizer |
| Butyl Acetate | 31.50 | solvent |
| Ethyl Acetate | 9.00 | solvent (to speed dry) |
| Ethyl Alcohol | 6.40 | diluent-(coupling agent) |
| Butyl Alcohol | 1.10 | diluent-(coupling agent) |
| Toluene | 21.00 | diluent |
| Colorant | 1.00 | |
| | 100.00 | |

Reports of allergy due to nail polish usage have been documented and attributed to the sensitization effects of resins such as the arylsulfonamide/formaldehyde resins.

Attempts have been made to overcome this deficiency by substituting natural resins and polyesters as nitrocellulose modifiers in the manufacture of nail polishes. However, the result has been nail enamels having poor gloss and adhesion.

An object of the present invention is to overcome these disadvantages.

Another object of the invention is to produce hypo-allergenic nail polishes approximating the quality and characteristics of ordinary nail polishes.

Still another object of this invention is to produce a superior nail polish which is hypo-allergenic and can thus be utilized as a universal nail polish.

SUMMARY OF THE INVENTION

According to a feature of the invention, a nail polish is made from 92 to 96% film former, colorant, plasticizer and solvent ingredients; and 4 to 8% polyester resin. All percentages cited herein are percent by weight of the total composition unless otherwise specified.

According to another feature of the invention, the polyester resin is a reaction product of 2,2,4-trimethyl-1, 3-pentanediol, isophthalic acid-85, and trimellitic anhydride, and a catalyst.

According to another feature of the invention, the polyester resin used is a synthetic hard water-reducible "polyester resin" which is the reaction product of (40%-60%) 2,2,4-trimethyl-1, 3-pentanediol, (22-33%) isophthalic acid-85, and (16%-26%) trimellitic anhydride, and an 0.1 to 0.3% dibutyl tin oxide catalyst having an acid value of 75 to 85, preferably 78-82, and most preferably 80. The term acid value is the value determined by finding how many miligrams of KOH are needed to neutralize 1 gram of the resin (according to American Oil Chemists Society standard test CD3A63 set forth in Official and Tentative Methods of the American Oil Chemists Society, Second Edition, including additions and revisions, 1947-1963.

More specifically, according to a feature of the invention, the synthetic hard water-reducible "polyester resin" is made from (50.932%) 2,2,4-trimethyl-1, 3-pentanediol, (27.579%) isophthalic Acid-85, (21.303%) trimellitic anhydride, and (0.186%) dibutyl tin oxide catalyst, heated at 204° C. to obtain an acid value of 75-85, preferably 75-82, and most preferably 80.

According to another feature of the invention, the polyester resin is dissolved in a solvent to a viscosity of 150 centipoise as determined using a model LVF Brookfield Viscometer at 77° with a #3 spindle at 20 rpm. Preferably, the solvent is butyl acetate.

According to another feature of the invention, part of the ingredients utilize a solid acrylic copolymer as an extender for nitrocellulose.

According to another feature of the invention, the acrylic copolymer is 1-5% active Neocryl B-1000 (or its equivalent), a product of the Polyvinyl Chemical Industries. This is used as a replacement for part of the nitrocellulose in the formula.

These nail enamel preparations were compared to ones utilizing toluene sulfonamide/formaldehyde resin as the nitrocellulose modifier. Nail enamels utilizing features of the invention compared favorably to nail enamels using toluene sulfonamide/formaldehyde resin.

These and other features of the invention are pointed out in the claims. Other objects and advantages of the invention will be evident from the following detailed description.

DESCRIPTION OF PREFERRED EMBODIMENTS

According to an embodiment of the invention, a nail polish is formed preferably of the following by weight:

| | |
|---|---|
| Nitrocellulose film forming ingredients | 10 to 20% |
| Diluent | 2 to 6% |
| Plasticizers | 4 to 9% |
| Solvents | 38 to 50% |
| Drying speed-up agents | 7 to 11% |
| Gel | 15 to 20% |
| Colorants | .6 to 5.0% |
| Polyester Resin | 4 to 8% |

The polyester resin is a product obtained from a mixture of 2,2,4-trimethyl-1, 3-pentanediol, isophthalic acid-85, and trimellitic anhydride. The reactant is formed by combining these three constituents in the presence of a catalyst, such as a dibutyl tin oxide catalyst.

The polyester resin is formed to have an acid value of 75-85, preferably 78-82, and most preferably 80±0.2. The acid value of 80±0.2 is critical for producing a nail lacquer of desired gloss and color. Acid values between 78 and 82 are acceptable for most purposes but produce lacquers somewhat less glossy and exhibit slight discoloration. Acid values between 75-78 and between 82-85 result in somewhat less desirable but still acceptable lacquers. Acid values outside these ranges result in poor color with cmparatively dark appearance generally unacceptable for nail polishes. As the acid value departs from 80, the lacquer becomes less viscous but remains acceptable until it falls outside the 75 to 85 range.

As used in this application, the acid value is the amount of unreacted acidity in the resin as measured by the number of milligrams of KOH needed to neutralize 1 gram of the polyester resin. The acid value is measured by American Oil Chemists Society Test CD3A63, in Official and Tentative Methods of the American Oil Chemists Society, Second Edition, including Additions and Revisions, 1947-1963 inclusive.

The procedure for forming the polyester resin is as follows: charge the 2,2,4-trimethyl-1, 3-pentanediol and the isophthalic acid-85 in a kettle and heat to melt. Begin agitation, equip kettle for reflux processing at 104° C. Charge dibutyl tin oxide catalyst and continue heating to 204° C. over a two to two and one half hour period, then return the decomposition product to the kettle. Hold for an acid value of 6 to 8. Cool to 160° C. and add trimellitic anhydride. Heat to 185° C. over a one and a half hour period while continuing to return the decomposition product to the kettle. Hold for an acid value of 100. At an acid value of 100, remove decomposition product with distillate and hold for an acid value of 80. Drop from kettle at 100% NVM.

The polyester resin preferably has a viscosity of 125 to 175 centipoise in the solvent, e.g., butyl acetate, as measured by a Model LVF Brookfield Viscometer available from Brookfield Engineering Laboratories, Inc. of Stoughton, Massachusetts, at 77°, #3 spindle at 20 rpm. Preferaby, the viscosity is 140 to 160 centipoise and most preferably 150±2. The viscosity of 150±2 is critical for obtaining the best results. Viscosity outside this range produces clouding and decreases gloss which is acceptable for most purposes in the range of 140 to 160 and acceptable for fewer purposes in the range 125 to 175 centipoise. Viscosities outside the latter range produce unacceptable results for nail enamel.

According to another embodiment of the invention, polyester resin is made from 40%-60%, 2,2,4-trimethyl-1, 3-pentanediol, 22%-33% isophthalic acid-85, and trimellitic anhydride.

The polyester is formed by combining the constituents with 0.1 to 0.3 dibutyl tin oxide as a catalyst. Other catalysts may be used. It is formed to have the aforementioned acid values and viscosities.

According to a preferred embodiment of the invention, the polyester is formed of 47 to 54%, 2,2,4-trimethyl-1, 3-pentanediol, 25 to 29% isophthalic acid-85, and 19 to 24% trimellitic anhydride. It is formed with 0.14-0.23% dibutyl tin oxide as a catalyst.

According to a more preferred embodiment of the invention, the polyester resin is formed of 50.932±0.001% 2,2,4-trimethyl-1, 27.579%±0.001% isophthalic acid-85, 21.303±0.001% trimellitic anhydride. Dibutyl tin oxide in the amount of 0.186±0.001% is used as a catalyst.

According to another embodiment of the invention, the ingredients of the above polyester resin are combined in stoichiometric amounts.

According to another embodiment of the invention, 1 to 3.5% solid acrylic copolymer, such as that available under the trademark Neocryl B-1000 from Polyvinyl Chemical Industries, Wilmington, Mass., is used as an extender for nitrocellulose at 10 to 30% replacement. This extender further exhances the gloss and flexibility of the system. Evaluations in the laboratory and on fingernails demonstrated improved gloss and wear.

Neocryl B-1000 is a solid acrylic copolymer designed for use an an extender for nitrocellulose in clear and pigmented coatings for metal, wood, paper, and ink applications. It is readily soluble in solvents commonly used with nitrocellulose lacquers including various exempt solvent systems. Extensive testing in typical nitrocellulose formulas indicates 20-30 percent of B-1000 can be substituted as a direct replacement for nitrocellulose without compromising performance properties. It is:

Compatible with nitrocellulose,
Compatible with other lacquer vehicles,
Easily and Rapidly dissolved, and
Soluble in exempt solvent blends.

It has the following typical physical properties:

| As supplied: | |
|---|---|
| Form | Free-flowing, non-dusting beads |
| Nonvolatile weight | 98% Minimum |
| Specific Gravity @ 25° C. | 1.05 |
| Bulking Value @ 25° C. | 0.114 gal./lb. |
| Hardness, Tukon | 11-13 KHN |
| solids solution in toluene: | |
| Viscosity, cps Brookfield @ 25° C. | 350 |
| Color | Light Yellow |
| Clarity | Excellent |

Its typical film properties are:

| Dry Film Cast From Solvent (Toluene 30%) | |
|---|---|
| Dry Time, Min., 3 Mil Wet | 15 |
| Appearance | Clear, glossy |
| Character | Continuous, hard, tough, flexible |
| Hardness (7 day) | |
| Sward | 66 |
| Pencil | 4H |
| Impact Resistance, in.-lb. | |
| On Bonderite 100 steel | |
| Direct, P/F | 70/80 |
| Reverse, P/F | 20/30 |
| Flexibility, in. (Pass) | 8 |
| conical mandred on | |
| Bonderite 100 steel | |
| QUV Ultraviolet Exposure Test | |
| 5 days | Trace yellow |
| 3 weeks | Slight yellow |

The solubility in various solvents is listed below:

| | Solubility (40% T.S.) |
|---|---|
| n-butyl Acetate | S |
| Methyl Ethyl Ketone | S |
| Toluene | S |
| Xylene | S |
| Acetone | S |
| Methyl Isobutyl Ketone | S |
| VM + P Naphtha | I |
| Isopropanol | I |
| n-Butanol | I |
| Ethanol | I |

Solvent tolerance is a measure of reducibility with a secondary solvent after the product is cut in a primary solvent. It can aid the formulator in choosing the optimum solvent blend for exempt solvent systems. The solvent tolerance of a 40% solids Neocryl B-1000 solution in toluene is given below as cc's of solvent added to the solution without causing a perceptible haze.

| SOLVENT TOLERANCE | |
|---|---|
| Solvent | Tolerance[1] |
| Acetone | Infinite |
| High Flash Naphtha | Infinite |
| Isopropanol | 7 |
| n-Butanol | 11 |
| Ethanol (200 Proof) | 10 |
| Ethanol (190 Proof) | 4 |
| VM + P Naphtha | 6 |

[1]cc's of solvent/10 gms. of 40% Neocryl B-1000 in Toluene.

According to another embodiment of the invention, the nail lacquer is preferably composed of the following ingredients:

| | % |
|---|---|
| Nitrocellulose RS ½ sec. | 4-6 |
| Nitrocellulose RS ¼ sec. | 6-10 |
| Isopropyl Alcohol | 2-6 |
| Camphor | 1-3 |
| Dibutyl Phthalate | 3-6 |
| Butyl Acetate | 15-25 |
| "Polyester Resin" | 4-8 |
| Toluene | 15-25 |
| Bentone gel (6.25%) | 15-20 |
| Nitrocellulose lacquer base | |
| Ethyl Acetate | 7-11 |
| Guanine 11% in lacquer base | 0.5-1.0 |
| Iron Oxides | 0.05-.09 |
| D & C Red #6 Barium Lake | 0.10-.14 |
| Titanium Dioxide | 0.50-.60 |
| D & C Red #7 Calcium Lake | 0.04-.06 |
| Ferric Ferrocyanide | 0.001-0.003 |

The Bentone (6.25%) gel is preferably in the form sold by NL Industries, of Heightstown, N.J. 08520 under the name Bentone 27, the trademark for its stearalkonium hectorite.

In the above, the nitrocellulose constitutes the film forming ingredient, the isopropyl alcohol and toluene the diluent, the camphor and dibutyl phthalate the plasticizer, the butyl acetate the solvent, ethyl acetate a drying speed-up agent, the Bentone the gel, the guanine, iron oxides, D & C Red, titanium dioxide, D & C Red #7, and ferric ferrocyanide the colorants.

According to another embodiment of the invention, the nail polish is composed of the following:

| | % |
|---|---|
| Nitrocellulose RS ¼ sec. Wet (70% in Isopropyl Alcohol) | 6-12 |
| Nitrocellulose RS ⅜ sec. Wet (70% in Isopropyl Alcohol) | 3-6 |
| Solid Acrylic Copolymer, e.g. Neocryl B-1000 or equivalent | 1-5 |
| Butyl Acetate | 20-30 |
| Toluol | 20-30 |
| Ethyl Acetate | 7-10 |
| Camphor | .5-2 |
| Bentone gel (6.25%) | 12-22 |
| Dibutyl Phthalate | 2-6 |
| Benzophenone-1 | .05-2 |
| "Polyester Resin" | 3-10 |
| Iron Oxides | .2-.8 |
| Titanium Dioxide | .2-.8 |
| D & C Red #6 Barium Lake | .05-.15 |
| D & C Red #7 Calcium Lake | .01-.07 |
| Ferric Ferrocyanide | .02-.07 |

(Neocryl B-1000 is the registered Trademark of Polyvinyl Chemical Industries, Wilmington, Massachusetts.)

In both of these embodiments, the polyester resin is composed of the aforementioned ingredients in varying amounts.

The following are examples of lacquers made according to the invention:

EXAMPLE I

|  | % |
| --- | --- |
| Nitrocellulose RS ½ sec. | 4.43 |
| Nitrocellulose RS ¼ sec. | 8.87 |
| Isopropyl Alcohol | 5.70 |
| Camphor | 1.00 |
| Dibutyl Phthalate | 6.00 |
| Butyl Acetate | 19.50 |
| "Polyester Resin" | 5.81 |
| Toluene | 18.5 |
| Ethyl Acetate | 7.953 |
| Bentone 27 (6.25%) gel | 21.00 |
| Nitrocellulose lacquer base | |
| Guanine 11% in lacquer base | 0.82 |
| Iron Oxides | 0.07 |
| D & C Red #6 Barium Lake | 0.12 |
| Titanium Dioxide | 0.55 |
| D & C Red #7 Calcium Lake | 0.045 |
| Ferric Ferrocyanide | 0.002 |
| | 100.00 |

In this example, a mechanical stirrer was used and the diluent isopropyl alcohol was added first. This was followed by the solvents toluene, then butyl acetate, the plasticizers camphor and dibutyl phthalate, the film forming ingredients nitrocellulose, the polyester resin and the Bentone gel (6.25%). Agitation is continued in stainless steel or aluminum vessels or until the solution is complete. The clear lacquer is then passed through a filter to remove any insolubles. This improves its clarity and brilliance and insures a glossier film. Pigmented enamels are then prepared by adding the appropriate amount of colorants in the form of a paste or concentrate under agitation to the clear lacquer in the mixing tank and color matched to a standard lab master.

Laboratory evaluations were performed to examine the gloss, flow characteristics, compatability of constituents during drying, drying rate, and wear resistance.

EXAMPLE II

|  | % |
| --- | --- |
| Nitrocellulose RS ¼ sec. Wet (70% in Isopropyl Alcohol) | 12.0 |
| Nitrocellulose RS ½ sec. Wet (70% in Isopropyl Alcohol) | 6.0 |
| Neocryl B-1000 | 1.50 |
| Butyl Acetate | 19.65 |
| Toluol | 18.00 |
| Ethyl Acetate | 8.75 |
| Camphor | .85 |
| Bentone 27 (6.25%) gel | 21.00 |
| Dibutyl Phthalate | 4.00 |
| Benzophenone-1 | 0.10 |
| "Polyester Resin" | 7.00 |
| Iron Oxides | 0.47 |
| Titanium Dioxide | 0.49 |
| D & C Red #6 Barium Lake | 0.10 |
| D & C Red #7 Calcium Lake | 0.04 |
| Ferric Ferrocyanide | 0.05 |

The ingredients were treated as in Example 1, except that the Neocryl B-1000 was added following the nitrocellulose. The polyester resin was formed from: (50.932%), 2,2,4-trimethyl-1,3-pentanediol, (27.579%), isophthalic acid-85, (0.186%), dibutyl tin oxide and (21.303%), trimellitic anhydride using the procedure of Example 1.

While the embodiments of the invention have been described in detail, it will be evident to those skilled in the art, that the invention may be embodied otherwise without departing from its spirit and scope.

In the examples and claims which follow, all compositions are given in weight percentages of the total weight. Temperatures are given in Centigrade.

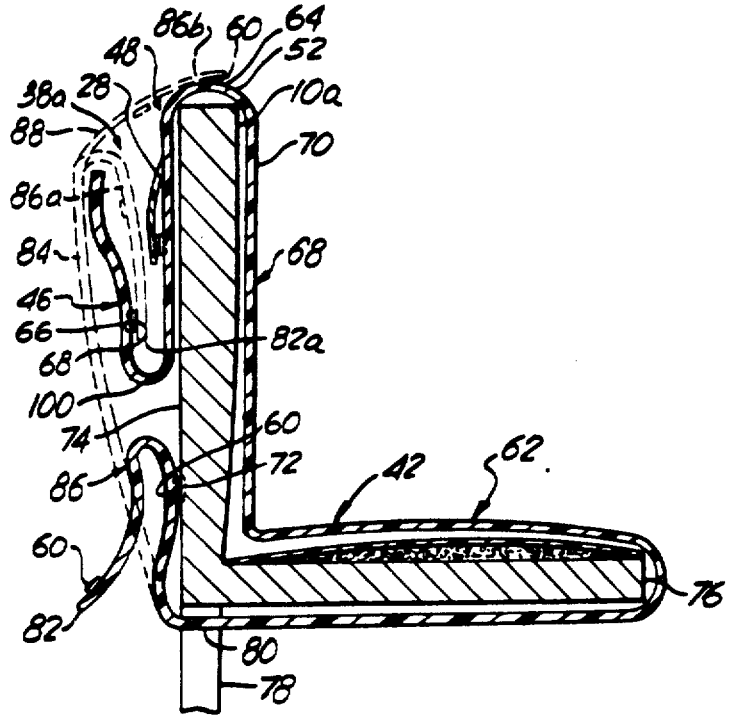

What is claimed is:

1. A nail polish formed from 92% to 96% of ingredients including a film former, colorant, plasticizer, and solvent; and 4% to 8% polyester resin, P1 said polyester resin being formed from 2,2,4-trimethyl-1, 3-pentanediol, isophthalic acid-85, and trimellitic anhydride.

2. A nail polish as in claim 1, wherein said polyester resin is formed of 40-60% 2,2,4-trimethyl-1, 3-pentanediol, 22%-33% isophthalic acid-85, 0.1%-0.3% dibutyl tin oxide catalyst, and 16-26% trimellitic anhydride.

3. A nail polish as in claim 2, wherein said polyester resin is formed of 50.932+0.001% 2,2,4-trimethyl-1, 3-pentanediol, 27.579±0.001% ispthalic acid-85, 0.186±0.001% dibutyl tin oxide catalyst and 21.303±0.001% trimellitic anhydride.

4. A nail polish as in claim 2, wherein said polyester resin has an acid value of 78-82.

5. A nail polish as in claim 3, wherein said polyester resin has an acid value of 80±0.2.

6. A nail polish as in claim 2, wherein said polyester resin has a viscosity of 140-150.

7. A nail polish as in claim 3, wherein said polyester resin has a viscosity of 150±2.

8. A nail polish as in claim 4, wherein said polyester resin has a viscosity of 140-160.

9. A nail polish as in claim 5, wherein said polyester resin has a viscosity of 140±0.2.

10. A nail polish as in claim 2, wherein said polyester resin has an acid value of 75-85.

11. A nail polish as in claim 3, wherein said polyester resin has an acid value of 75-85.

12. A nail polish as in claim 1, wherein said polyester resin has an acid value of 78-82.

13. A nail polish as in claim 3, wherein said polyester resin has an acid value of 78-82.

14. A nail polish as in claim 1, wherein said polyester resin has an acid value of 80±0.2.

15. A nail polish as in claim 2, wherein said polyester resin has an acid value of 80±0.2.

16. A nail polish as in claim 2, wherein said polyester resin has a viscosity of 125-175.

17. A nail polish as in claim 3, wherein said polyester resin has a viscosity of 125-175.

18. A nail polish as in claim 1, wherein said polyester resin has a viscosity of 140-160.

19. A nail polish as in claim 3, wherein said polyester resin has a viscosity of 140-160.

20. A nail polish as in claim 1, wherein said polyester resin has a viscosity of 150±2.

21. A nail polish as in claim 2, wherein said said polyester resin has a viscosity of 130±2.

22. A nail polish formed from 92% to 96% of ingredients including nitrocellulose, colorant, plasticizer, and solvent; and 4% to 8% polyester resin,
   said polyester resin being formed from 2,2,4-trimethyl-1, 3-pentanediol, isophthalic acid-85, and trimellitic anhydride,
   said polyester resin having an acid value of 75 to 85 and a viscosity of 125 to 175.

23. A nail polish as in claim 22, wherein said polyester resin is formed of 40-60% 2,2,4-trimethyl-1, 3-pentanediol, 22%–33% isophthalic acid-85, 0.1%–0.3% dibutyl tin oxide catalyst, and 16–26% trimellitic anhydride.

24. A nail polish as in claim 22, wherein said polyester resin is formed of 50.932±0.001% 2,2,4-trimethyl-1,3-pentanediol, 27.579±0.001% isophthalic acid-85, 0.186±0.001% dibutyl tin oxide catalyst and 21.303±0.001% trimellitic anhydride.

25. A nail polish as in any one of claims 1 to 3, 4, 5, 6, 7, 8, 9, and 10–24, wherein said film former, colorant, plasticizer and solvent ingredients consist of nitrocellulose, isopropyl alcohol, camphor, dibutyl phthalate, butyl acetate, toluene, ethyl acetate and bentone 27.

26. A nail polish as in any one of claims 1 to 3, 4, 5, 6, 7, 8, 9, and 10–24, formed from the following percentages by weight of the total:

| | |
|---|---|
| Nitrocellulose RS ½ Sec. | 2–4 |
| Nitrocellulose RS ¼ Sec. | 4–8 |
| Isopropyl Alcohol | 2–6 |
| Camphor | 1–3 |
| Dibutyl Phthalate | 3–6 |
| Butyl Acetate | 15–25 |
| "Polyester Resin" | 4–8 |
| Roluene | 15–25 |
| Ethyl Acetate | 7–11 |
| Bentone gel (6.25%) | 15–20 |
| Nitrocellulose lacquer base | |
| Guanine 11% in lacquer base | 0.5–1.0 |
| Iron Oxides | 0.05–.09 |
| D & C Red #6 Barium Lake | 0.10–.14 |
| Titanium Dioxide | 0.50–.60 |
| D & C Red #7 Calcium Lake | 0.04–.06 |
| Ferric Ferrocyanide | 0.001–0.003 |

27. A nail polish as in any one of claims 1 to 3, 4, 5, 6, 7, 8, 9, and 10–24, formed from the following by weight:

| | |
|---|---|
| Nitrocellulose RS ¼ Sec. Wet (70% in Isopropyl Alcohol) | 4–8% |
| Nitrocellulose RS ½ Sec. Wet (70% in Isopropyl Alcohol) | 2–4% |
| Solid Acrylic Copolymer | 1–4% |
| Butyl Acetate | 20–30% |
| Toluol | 20–30% |
| Ethyl Acetate | 7–10% |
| Camphor | .5–2% |
| Bentone gel (6.25%) | 12–22% |
| Dibutyl Phthalate | 2–6% |
| Benzophenone-1 | .05–2% |
| "Polyester Resin" | 3–10% |
| Iron Oxides | .2–.8% |
| Titanium Dioxide | .2–.8% |
| D & C Red #6 Barium Lake | .05–.15% |
| D & C Red #7 Calcium Lake | .01–.07% |
| Ferric Ferrocyanide | .02–.07% |

28. A nail polish as in any one of claims 1 to 3, 4, 5, 6, 7, 8, 9, and 10–24, formed from:

| | |
|---|---|
| Nitrocellulose RS ½ Sec. | 5.1% |
| Nitrocellulose RS ¼ Sec. | 10.2% |
| Isopropyl Alcohol | 6.7% |
| Camphor | 0.93% |
| Dibutyl Phthalate | 5.83% |
| Butyl Acetate | 17.00% |
| "Polyester Resin" | 7.00% |
| Toluene | 16.53% |
| Ethyl Acetate | 8.95% |
| Bentone gel (6.25%) | 21.00% |
| Nitrocellulose lacquer base | |
| Guanine 11% in lacquer base | 0.82% |
| Iron Oxides | 0.07% |
| D & C Red #6 Barium Lake | 0.12% |
| Titanium Dioxide | 0.55% |
| D & C Red #7 Calcium Lake | 0.045% |
| Ferric Ferrocyanide | 0.002% |
| | 100.00% |

29. A polish as in any one of claims 1 to 3, 4, 5, 6, 7, 8, 9, or 10–24, formed from:

| | |
|---|---|
| Nitrocellulose RS ¼ Sec. Wet (70% in Isopropyl Alcohol) | 10.0% |
| Nitrocellulose RS ½ Sec. Wet (70% in Isopropyl Alcohol) | 5.0% |
| Neocryl B-1000 | 2.68% |
| Butyl Acetate | 20.00% |
| Toluol | 19.32% |
| Ethyl Acetate | 8.75% |
| Camphor | .85% |
| Bentone gel (6.25%) | 21.00% |
| Dibutyl Phthalate | 4.00% |
| Benzophenone-1 | 0.10% |
| "Polyester Resin" | 7.00% |
| Iron Oxides | 0.47% |
| Titanium Dioxide | 0.49% |
| D & C Red #6 Barium Lake | 0.10% |
| D & C Red #7 Calcium Lake | 0.04% |
| Ferric Ferrocyanide | 0.05%. |

* * * * *

UNITED STATES PATENT AND TRADEMARK OFFICE
CERTIFICATE OF CORRECTION

PATENT NO. : 4,302,046            Page 1 of 2

DATED : Nov. 24, 1981

INVENTOR(S) : Esther Lazazzero

It is certified that error appears in the above-identified patent and that said Letters Patent is hereby corrected as shown below:

On the title page the illustrative drawing should appear as per the attached sheet.

Signed and Sealed this

Twenty-ninth Day of March 1983

[SEAL]

*Attest:*

GERALD J. MOSSINGHOFF

*Attesting Officer*      *Commissioner of Patents and Trademarks*

United States Patent [19]

Lazazzero

[11] 4,302,046
[45] Nov. 24, 1981

[54] PURSE HOLDER

[76] Inventor: Esther Lazazzero, 86 Greenlawn Ave., Clifton, N.J. 07013

[21] Appl. No.: 963,482

[22] Filed: Nov. 24, 1978

Related U.S. Application Data

[63] Continuation-in-part of Ser. No. 685,727, May 12, 1976, abandoned.

[51] Int. Cl.³ .................................................. A47C 7/62
[52] U.S. Cl. ................................. 297/191; 224/275; 297/219; 297/229
[58] Field of Search .......................... 150/34; 224/275; 297/188, 191, 219, 229, 231

[56] References Cited

U.S. PATENT DOCUMENTS

| 1,279,915 | 9/1918 | Rogers | 150/34 |
| 2,223,532 | 12/1940 | Sallop | 297/191 X |
| 2,703,426 | 3/1955 | Barkl | 297/191 X |
| 3,014,759 | 12/1961 | Bing | 297/191 |
| 3,151,909 | 10/1964 | Gerdetz | 297/188 |
| 3,479,085 | 11/1969 | Weinstein | 297/219 |

FOREIGN PATENT DOCUMENTS

| 174850 | 2/1922 | United Kingdom | 297/119 |
| 1476493 | 6/1977 | United Kingdom | 297/191 |

*Primary Examiner*—William E. Lyddane
*Attorney, Agent, or Firm*—Robert D. Farkas

[57] ABSTRACT

This disclosure pertains to a slip cover device adapted to be positioned over the uppermost portions of a chair backrest. The open mouth portion of an inverted U shaped cross-section fabricated from a flexible material is applied downwardly surrounding the uppermost marginal edges of the backrest of the chair. The rearmost surface of the cover is provided with a pouch having an open mouth at the uppermost region thereof. A purse may be stored in the pouch, utilizing a flexible strip hingeably affixed at one end and removably affixed at the other end to the rearmost surface of the cover to capture the handle of the purse. One marginal edge of the inverted U shaped cross-section, that is applied downwardly surrounding the uppermost marginal edges of the backrest of the chair, is elongated, such that the elongated portion may be attached to selected areas of the chair itself or the pouch portions of the apparatus or the portion of the apparatus which resides on the top of the backrest of the chair.

10 Claims, 4 Drawing Figures